United States Patent [19]

Schmidt et al.

[11] Patent Number: 4,777,317

[45] Date of Patent: Oct. 11, 1988

[54] PROCESS FOR POLYPROPENE MANUFACTURE

[75] Inventors: Gregory E. Schmidt, Batavia; James S. Moore, Brighton, both of Ill.

[73] Assignee: Amoco Corporation, Chicago, Ill.

[21] Appl. No.: 20,016

[22] Filed: Feb. 27, 1987

[51] Int. Cl.[4] .............................................. C07C 2/02
[52] U.S. Cl. .................................................. 585/532
[58] Field of Search ........................................ 585/532

[56] References Cited

U.S. PATENT DOCUMENTS 4,528,414  7/1985  Long et al. ...................... 585/528

OTHER PUBLICATIONS

Olah, *Friedel–Crafts and Related Reactions*, Interscience Publishers (1963), pp. 88–90 & 207–209.

*Primary Examiner*—Curtis R. Davis
*Attorney, Agent, or Firm*—Matthew R. Hooper; William H. Magidson; Ralph C. Medhurst

[57] ABSTRACT

Continuous Friedel-Crafts polymerization of propylene based feedstock in a polypropene reactor system to obtain viscous polypropene having a viscosity within the range of about 2 to about 200 centistokes, comprising: (a) continuously injecting water into the feed or the reactor at a monitored and controlled rate and (b) periodically increasing or decreasing the rate of water injection in response to deviations in the molecular weight of the polypropene product from a desired molecular weight.

25 Claims, 3 Drawing Sheets

PROCESS FOR POLYPROPENE MANUFACTURE

The present invention relates generally to cationic polymerization of propylene-based feedstocks to obtain a viscous liquid olefin polymer commonly referred to as "polypropene." In particular, the invention concerns an improved method and apparatus for controlling the molecular weight of polypropene product output from a polypropene reactor system which utilizes a Friedel-Crafts polymerization catalyst.

It has long been known that normally gaseous olefins such as propylenes, butylenes or mixtures thereof can be converted to viscous liquid polymers using Freidel-Crafts catalyst or Lewis acid catalyst. Such polymerization can be carried out, with or without the presence of a promoter, to prepare low molecular weight polypropenes of approximately 200–3000 Mn. The chemical literature includes a number of examples of propylene polymerization to produce polypropenes using aluminum halide catalyst in conjunction with a variety of promoters. See, e.g., C. M. Fontana, Journal of the American Chemical Society, 70, 3745 (1948).

Polypropenes are odorless, oxidation-resistant viscous liquid polymers having various industrial applications. For example, polypropenes are widely used as reactive intermediates in the preparation of basic alkyl sulfonate detergents and anti-rust agents useful for manufacture of petroleum additives. In addition, polypropenes are commonly used as plasticizing agents for adhesive and rubber compounds, and as process acids in the manufacture of thermoplastic elastomers.

Molecular weight is perhaps the most important specification for commercial grade polypropenes. Using on-line monitoring and control of selected operating conditions of a polypropene reactor system, a range of viscous polymer products can be obtained having molecular weights of approximately 200 to 3000. Such monitoring and control is desirably maintained automatically or semi-automatically by feeding monitored conditions electronically to a microprocessor-equipped controller which then adjusts one or more of the selected conditions to achieve the target molecular weight. Such continuous monitoring and adjustment is typically referred to as "feedback control."

Unfortunately, from a manufacturing standpoint, it is not practical to continuously monitor the molecular weight of polypropene product output from a polypropene reactor. Conventional laboratory techniques for determining molecular weight involve relatively long procedures unsuitable for the type of continuous monitoring required in a feedback control system.

In view of this problem, rather than monitor molecular weight, per se, it is generally preferred instead to continuously monitor the viscosity of the polypropene output during manufacture. As is well known, mathematical relationships between molecular weight and viscosity can be used to predict the molecular weight of a given polypropylene product when its viscosity is known, other variables remaining constant.

In view of the importance of maintaining a desired target viscosity, and thus molecular weight, of the polypropene product from a polypropene reactor system, it is important to know which process variables or conditions of such an operating system affect the polypropene viscosity. Once such outcome-determining variables are known, mathematical relationships between the viscosity and such variables can be derived and utilized with confidence in an automated, preferably computerized, feedback control system for polypropene manufacture.

It is already well known that the viscosity of liquid olefin polymers can be reduced by increasing the reactor temperature. See e.g., Nichols U.S. Pat. No. 3,200,169 and Schmidt et al. U.S. Pat. No. 4,620,049. Schmidt et al. further disclose the addition of moisture to the reactor or the feed of a polybutene reactor system to reduce the viscosity of the product output. Hersberger, Canadian Pat. No. 470,466 discloses that increasing isobutylene concentration lowers molecular weight in polypropene manufacture.

While lowering the reaction temperature is a useful way of increasing the viscosity and molecular weight of the polymer product, doing so places an increased demand on refrigeration equipment used to cool the reactor, can result in higher energy consumption, and thus can have a negative impact, in terms of economics, on the overall process. Also, safety becomes an increasing concern as greater demands are placed on refrigeration equipment used to cool the polypropene reactor.

Given the costs associated with lowering reactor temperature to increase the viscosity of polymer product, and also in view of the energy requirements of reactor cooling regardless of the product viscosity desired, it is advantageous to identify operating conditions, other than reactor temperature, which can be used to control viscosity, and particularly such conditions which can be controlled to increase the viscosity without need for a reduction in reactor temperature.

Moreover, the ability to control variables other than temperature, or feed concentration, as a means of controlling viscosity, also provides a benefit in manufacturing low molecular weight (low viscosity) polypropene. This is true insofar as the lower limit of polypropene molecular weight is generally set by the maximum temperature and pressure at which a given polypropene reactor system can be safely operated. The ability to control molecular weight by adjusting variables other than reactor temperature permits further reduction in the molecular weight of polypropene below the lower limit possible in a given reactor system.

Finally, insofar as it is known that changing the isobutylene concentration of the propylene feed changes the molecular weight of the polypropene product, it is beneficial to be able to identify and control other variables in the polypropene reactor system such that, depending upon the relative costs of propylene and isobutylene, occasional adjustments in the relative concentrations of these feed components can be effected to maximize use of cheaper feeds without changing the molecular weight of the product output.

Accordingly, general object of the present invention is to provide an improved method and apparatus for controlling the molecular weight of polypropenes wherein operating conditions other than, or in addition to, reactor temperature and feed concentration can be monitored and adjusted in order to maintain the polypropene product at a desired molecular weight, preferably using the cheapest available feedstocks. Other objects appear hereinafter.

We have now found that the objects of the present invention are, obtained in a continuous Friedel-Crafts polymerization of propylene based feedstock in a polypropene reactor system to obtain viscous polypropene having a viscosity in the range of about 2 to about 200 centistokes at 210° C. comprising (a) continuously injecting water into the feed or the reactor at a monitored and controlled rate and (b) periodically adjusting the rate of water injection in response to deviations in the molecular weight of polypropene product from a desired molecular weight. The above process preferably further comprises the steps of monitoring and controlling the reactor residence time and periodically increasing or decreasing the residence time in response to deviations in the molecular weight of the polypropene product from a desired molecular weight.

The present invention is based upon our discovery that changes in either the water content of the feed (or reactor) or the residence time of the feed in the reactor can change the molecular weight of polypropene product from a polypropene reactor system.

More specifically we have found that increasing either the water concentration in the feed (or the reactor) or the residence time of the feed in the reactor will result in an increase in the molecular weight of the product output. The opposite effect is observed if the moisture level or residence time is decreased. We find this phenomenon particularly surprising and unexpected in view of our previous discovery (see commonly assigned Schmidt et al. U.S. Pat. No. 4,620,049) that addition of moisture to the feed or reactor lowers molecular weight in the manufacture of the polybutenes, and that residence time has little effect on polybutene viscosity.

Among the advantages of the present invention is that it permits upward adjustments in product molecular weight with little or no need to correspondingly adjust downward the reactor temperature. Adding moisture to the feed or reactor, or increasing the reactor residence time, or effecting a combination of these steps, results in a higher molecular weight product for a given reactor temperature, with a resultant energy savings.

Another advantage of the invention is that the relative concentrations of $C_3$ and $C_4$ components in the feed can be adjusted in response to fluctuations in the market price of suitable feeds without causing a deviation from a target molecular weight of polypropene product. This permits the polypropylene system to maximize use of the cheapest available feeds in manufacturing a particular product. For example, if it is desired to decrease the concentration of a more expensive $C_4$ feed component while increasing the amount of less expensive feeds, the resulting increase in polypropene molecular weight can be offset by downward adjustments in the reactor or feed water concentration or in the reactor residence time in accordance with the present invention.

The present invention is also directed to a polypropene reactor system including a feedback control apparatus for controlling the molecular weight of viscous polypropene product output obtained from continuous Friedel-Crafts polymerization of propylene based feedstock in a polypropene reactor system, wherein the feedback control apparatus comprises: means for continuously monitoring the viscosity of the product output and for continuously monitoring operating variables of the system and adjusting said variables in response to deviations in product viscosity or molecular weight from a desired target value, said means including means for continuously monitoring the feed or reactor water content, or the reactor residence time, means for continuously injecting water into the feed or reactor at a monitored and controlled rate, and means for adjusting the water content or reactor residence time in response to deviations in the product viscosity or molecular weight from a desired target viscosity or molecular weight.

Given our discovery that water content of the feed (or reactor) and reactor residence time exert an affect upon polypropene molecular weight and viscosity independently of other process variables in propylene polymerization, it should be apparent to those skilled in the art that conventional non-linear regression techniques can be used to derive a formula, based on empirical data, which correlates polypropene product viscosity with feed moisture levels and/or reactor residence time. Accordingly, the present invention is further directed to a method for controlling the molecular weight of viscous polypropene product from cationic polymerization of a propylene based feed in a polypropene reactor system, the method comprising: (a) continuously injecting water into the feed or the reactor at a monitored and controlled rate; (b) determining the water content in the feed or reactor or the reactor residence time; (c) calculating a predicted molecular weight or viscosity of the polypropene product based upon an empirically derived formula correlating reactor system operating variables comprising feed or reactor water content or reactor residence time to product viscosity or molecular weight in order to determine if such predicted molecular weight or viscosity is equal to a desired molecular weight or viscosity; and (d) increasing or decreasing the rate of water injection into the feed or reactor, or increasing or decreasing the residence time such that the predicted viscosity or molecular weight is equal to the desired viscosity or molecular weight. Where an empirical formula is used to correlate the effects of water and reactor residence time upon product viscosity as disclosed in the present invention it is generally preferred to include in such a formula correlations for other reaction variables known to have an effect upon product viscosity such as feed composition (i.e., the feed concentrations of isobutylene, cis-2-butene, and non-reactive monomers) product stripping conditions, and reactor temperature. Use of an empirically derived correlation formula which takes into account as many controllable and outcome-affecting variables as are known, including those of the present invention, i.e., water content and reactor residence time, provides greater flexibility in manufacturing an "on-spec" product in terms of molecular weight. As stated above, such flexibility is particularly desirable where it permits substitution of less expensive feeds in response to fluctuations in the market price of available feeds, while allowing the molecular weight of the product to remain relatively unchanged.

It is contemplated that the benefits of the present invention can be realized in a propylene reactor system in which operating conditions are monitored and controlled continuously by a computerized feedback control system designed to maintain a target viscosity of product output based on an empirically derived formula correlating the viscosity of the product with various controllable operating conditions. The present invention is therefore further directed to a polypropene reactor system including a feedback control apparatus for controlling molecular weight of product output from Friedel-Crafts polymerization of propylene based feed on a polypropene reactor system comprising: a polypropene reactor; a control circuit coupled to the reactor and having programmed or stored therein an empirically derived formula which correlates product molecular weight as determined by product viscosity or other characteristics of the product output with controllable operating variables of the reactor system comprising residence time, or the feed or reactor water content; means coupled to the reactor and to the control circuit for sensing and monitoring the operating variables; means in the control circuit for determining, based on said empirical formula, an approximate molecular weight of the product output, and for determining if said molecular weight is different from a desired molecular weight; means for continuously injecting water into the feed or reactor at a monitored and controlled rate; means for controlling the residence time of the feed in the reactor; and means coupled to said control circuit and responsive to deviations in said approximated product molecular weight from said desired molecular weight to alter said water content or reactor residence time to obtain the desired product molecular weight.

The present invention is further directed to a continuous process for producing viscous polypropene via Friedel-Crafts polymerization of propylene based feed containing up to about 25 wt.% isobutylene in a polypropene reactor system wherein the polypropene product is maintained at a target viscosity within the range of about 2 to about 30 centistokes despite periodic changes in the feed isobutylene concentration, the process comprising (a) continuously injecting water into the feed or the reactor at a monitored and controlled rate; (b) periodically increasing or decreasing the feed isobutylene concentration as desired based upon the cost of isobutylene relative to other feed components; and (c) periodically increasing or decreasing the rate of water injection, or the residence time of the feed in the reactor, in response to deviations in the polypropene target viscosity caused by said increase or decrease in the feed isobutylene concentration, whereby the polypropene target viscosity is maintained.

Figure 1:
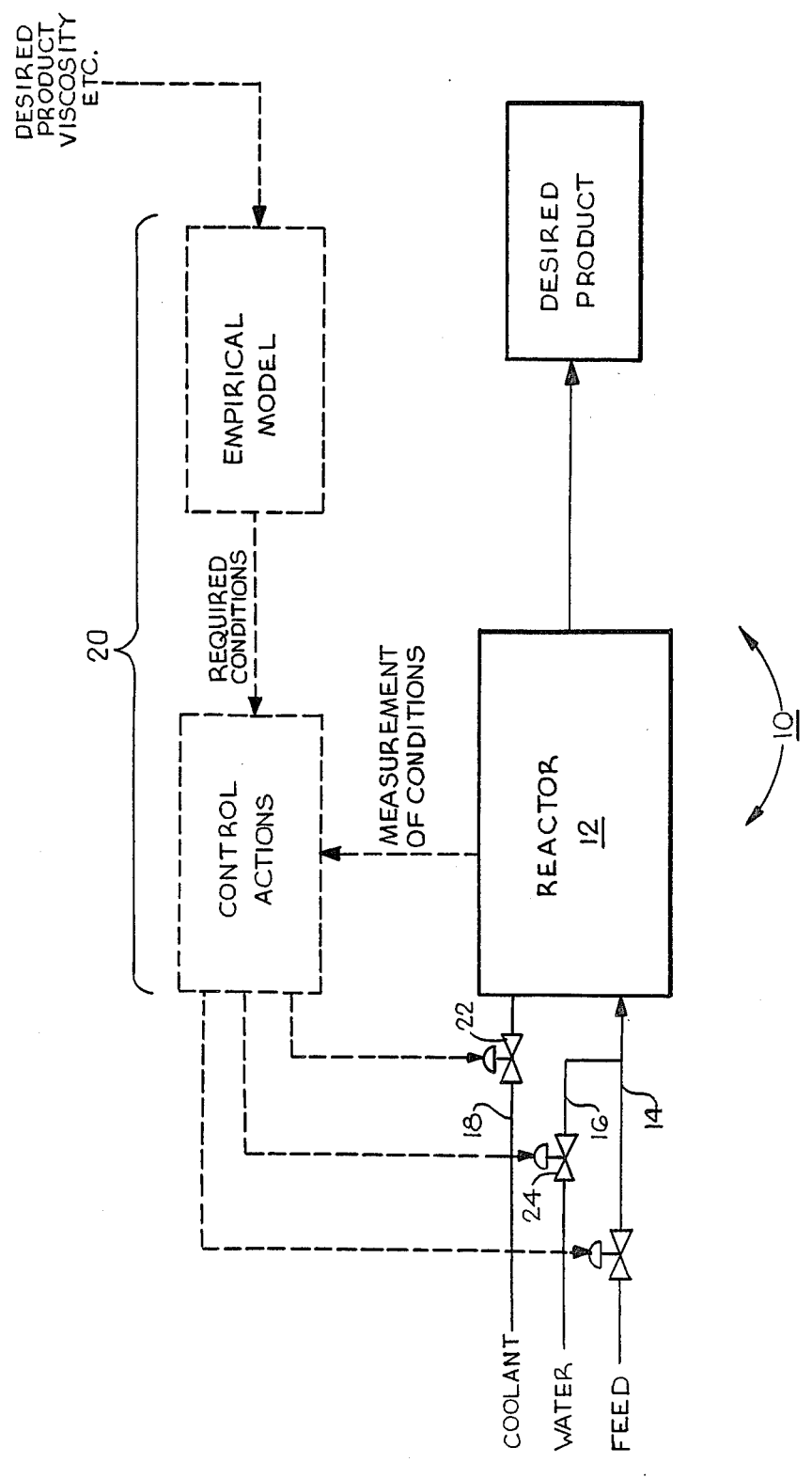
FIG. 1 is a block diagram of an apparatus or system according to the present invention for selectively controlling polypropene production.

Referring now to the drawings in greater detail, there is illustrated in FIG. 1 a polypropene reactor system 10 constructed according to the teachings of the present invention. The polypropene reactor system 10 includes a reactor 12 in which an exothermic reaction takes place as a result of the feeding of a propylene based feed stream via a feed input line 14, into the reactor 12. A catalyst can be fed into the reactor 12 via a catalyst input line (not shown). In view of the exothermic heat generated within the reactor 12, a refrigerant or coolant can be supplied via a coolant input line 18 to a jacket (not shown) situated around the reactor 12 or an internal heat exchanger situated in the reactor 12.

As is known in the art, a feed or stream of olefins are supplied to the reactor system. Depending upon the location of manufacture the olefins can be supplied to the reactor directly from a cracking tower for cracking a particular type of crude oil. The feed reacts with a cationic polymerization catalyst, preferably an aluminum halide, to produce in the reactor a viscous liquid polypropene polymer.

According to the teachings of the present invention, the reactor residence time (unit throughput) and/or the moisture levels in the feed (or reactor) are monitored and controlled. Moisture can be measured with a moisture analyzer and the residence time can be calculated by the control circuit 20 based on the rate of feed introduction into the reactor, the concentration of reactive monomers in the feed, and the volume of the feed in reactor.

Other operating conditions of the reactor system such as reaction temperature can also be monitored. The reaction temperature can be monitored with a thermocouple and changed by altering the flow of coolant to the reactor 12 through a coolant input line 18. The feed rate is controlled by valve 26 and the water content of the feed is controlled by valve 24.

The polypropene reactor system 10 of the present invention includes a control circuit 20 which can be realized by a microprocessor or computer with a memory including a ROM and a RAM. In the ROM is stored an empirical model of the reaction taking place within the reactor 12. A desired product viscosity or product molecular weight is supplied to the computer. This value of molecular weight is stored in the RAM and the empirical model is stored in the ROM of the memory.

The required conditions to obtain a desired molecular weight are calculated by the computer which then alters the level of water supplied to the reactor 12 or the feed 14 by operating a valve 24 in the water input line 16 and/or the residence time in the reactor 12 by operating a valve 26 in the feed input line 14, or the reaction temperature by operating a valve 22 in the coolant input line 18.

According to the present invention, the molecular weight of the desired product output of viscous polypropene can be controlled by measuring and monitoring controllable and result-affecting system variables comprising the water content of the feed or the reactor, and/or the residence time in the reactor. Then, the value of the water content of the feed or reactor, or the reactor residence time is plugged into a formula of the empirical model stored in the ROM of control circuit 20 relating water content in the feed or reactor and/or reactor residence time to produce molecular weight. A predicted molecular weight of the viscous polypropene product output can then be calculated and if this molecular weight varies from a desired target molecular weight the variables of water content in the feed or reactor, and/or reactor residence time can be adjusted by the computer or microprocessor in the control circuit 20.

The empirical formula can be determined using conventional regression analysis techniques applied to a large number of experiments measuring molecular weight of the product output for different feed reactor moisture levels or reactor residence times.

The viscous polypropene polymer produced by the reactor system 10 is preferably produced by polymerizing a propylene-based feed over a water-promoted cationic Friedel-Crafts catalyst, preferably aluminum chloride.

It should be noted here that the term propylene-containing feed means either a feed comprising primarily $C_3$ monomers, commonly referred to as a propane-propylene or "P—P" stream, or a mixed feed of $C_3$ monomers and $C_4$ monomers, such $C_4$ component being commonly referred to as a butane-butylene or "B—B" component. The $C_3$ component of the feed can be polymer grade propylene ($\approx$100% propylene), chemical grade propylene ($\approx$89-95% propylene), or refinery P—P ($\approx$30-70% propylene) or mixtures thereof. When preparing polypropenes with lower target viscosities it is generally desirable to combine the P—P feed with additional refinery B—B (40-70% isobutylene), olefins B—B ($\approx$89-95% isobutylene), or polymer grade isobutylene ($\approx$100% isobutylene), or mixtures thereof as such inclusion tends to have a viscosity-lowering effect on the polypropene product output. In any case, "propylene-based feed" is intended to mean a feed in which the reactive monomer(s) comprises at least about 25 wt% propylene, and preferably about 40 to about 100 wt.% thereof.

A propylene-containing feed for use in the present invention can contain propane, propylene, butane, 1-butene, isobutylene, trans-2-butene cis-2-butene and isobutane, etc. Most commonly, the propylene feed comes from refinery operations such as from a cracking tower, i.e., a tower for steam cracking or catalytic cracking. In the polypropene reactor system 10 of the present invention, the propylene stream is contacted with a water-promoted Friedel-Crafts catalyst, preferably, aluminum chloride, in the reactor 12 and the polymeric polypropene product is removed and separated from unreacted monomer. A similar system for polybutene manufacture is described in U.S. Pat. No. 3,501,551, incorporated by reference herein.

According to the present invention, feed (or reactor) moisture or reactor residence time can be intentionally changed to effect changes in the molecular weight of the polypropene product output. Preferably, the reactor temperature and feed concentration can also be monitored and controlled to control polypropene molecular weight. The feed concentration values found to effect the molecular weight of the polypropene product are the concentration of cis-2-butene, the concentration of isobutylene, and the concentration of inert monomers such as butane and propane. The concentration of propylene is not found to effect the molecular weight of the polypropene product output.

The actual values one can select for the system operating conditions such as reactor temperature, feed concentration, reactor pressure, moisture content of the feed, and reactor residence time are not critical to the present invention and can be chosen based on desired economic constraints and on the reactor design limits. The directional effects upon product molecular weight which result from changes in reactor residence time or feed moisture can be observed regardless of the values or changes in other system variables.

Although, generally speaking, the maximum reactor temperatures and pressures suitable for a polypropene reactor system are determined by the safe design limits of the reactor system, a preferred operating temperature range is from about 45° to 200° F. and a preferred pressure is in the range of about 100-250 psi. Insofar as the present invention is preferably directed to systems using water-promoted Friedel-Crafts catalyst, a lower practical limit on operating temperature is the point at which water begins to crystallize in the reactor, and/or becomes insoluble in the hydrocarbon reaction mixture. Most preferably the reaction temperature is from about 60° to about 140° and the reactor pressure is about 125 to 175 psi.

Preferably the feed moisture level is from about 10-500 ppm by weight of the feed. A minimum amount of water is generally needed to promote the catalyst. However, at moisture levels greater than about 500 ppm, problems are encountered due to reaction of the catalyst with the water which deactivates the catalyst. Preferred moisture levels are from about 100-300 ppm based on the feed. It is to be understood that the term "continuous injection of water" or "continuously injecting water" is intended to mean that the desired water concentration is maintained continuously in the reactor or the feed without excluding the possibility that actual injection of water into the feed or reactor may be discontinuous or incremental.

The reactor residence time is preferably from about 50 minutes to about 150 minutes and most preferably about 80-120 minutes, as determined by the most favorable economics for operation of the reactor system.

Feed concentration is also a factor in molecular weight of the polypropene product as discussed earlier. Preferably the feed isobutylene concentration is in the range of about 0 to about 20 wt.%; the feed cis-2-butene concentration is in the range of about 0-5 wt.%; and the feed inerts (defined as nonconvertible monomers, i.e., n-butane, isobutane, propane, etc.) are preferably in the range of about 15 to 60 wt.%.

It should be noted here that under normal operating conditions of a polypropene reactor system, i.e., at the temperatures and pressures mentioned above, it is generally difficult to manufacture lower molecular weight polypropenes (i.e. having viscosities in the range of about 2 to about 30 centistokes at 210° C.) unless isobutylene is included in the feed at concentrations of up to about 25 wt.% of the feed. Notwithstanding this fact, if the cost of $C_4$ feed components is cheaper than $C_3$ components, polypropene having a viscosity of from about 2 to about 60 centistokes (measured at 210° C.) can be manufactured from feedstocks in which the $C_4$ components (i.e. isobutylene, cis-2-butene and trans-2-butene) comprise up to about 75% by weight of the reactive (i.e. ethylenically unsaturated) monomers, provided the isobutylene concentration does not exceed about 50% by weight of the reactive monomers. The remaining reactive monomer is propylene in amount generally not less than about 25% by weight of the reactive monomers in the feed. At feed isobutylene concentrations greater than about 50 wt.% of the reactive monomers in the feed, and where the propylene concentration is less than about 25 wt.% of the reactive monomers, the manufacture of polybutene is favored. The effects of residence time and moisture content according to the present invention are not operative in polybutene manufacture.

Another very important distinction between polybutene manufacture and polypropene manufacture is that the conditions under which polypropene is manufactured generally result in conversion of at least about 75 wt%, and preferably at least about 95 wt.% of the ethylenically unsaturated monomers to polymeric material, and at least about 90 wt.% of the propylene in the feed is converted to polymer. One reason for this is that in polybutene manufacture generally about one-fifth to about one-third as much catalyst is employed than would be used for polypropene manufacture. Thus in the present invention it is generally preferred to use about 0.1 wt.% catalyst by weight of the feed, while in polybutene manufacture about 3 to 5 times that amount would be used. In polypropene manufacture where isobutylene is present in the feed essentially all of the isobutylene is polymerized, as contrasted with polybutene manufacture in which a substantial portion of the isobutylene in the feed is not polymerized and essentially none of the $C_3$ reactive monomers (including propylene) are polymerized.

An advantage of the present invention is that, in manufacture of lower molecular weight polypropenes where it is necessary or desirable to incorporate isobutylene in the feed, a desired target value of product viscosity can be maintained despite periodic intentional adjustments in the feed concentration of isobutylene, such adjustments being desirable from the standpoint of economics should the price of isobutylene increase or decrease relative to the other feed components used in polypropene manufacture. Despite such intentional periodic changes in the isobutylene concentration of the feed, a desired target viscosity of product can be maintained if, according to the present invention, the amount of water being injected into the feed (or the reactor), or the residence time of the feed in the reactor, is increased or decreased in response to, and to offset, deviations in the polypropene target viscosity caused by the intentional changes in the feed concentration of isobutylene.

Although not critical to the present invention, the temperatures at which polypropene product is stripped, as well as the catalyst concentration in the reactor, can affect product molecular weight and can be taken into consideration when controlling variables which control the product molecular weight. Lower stripping temperatures result in lower viscosity products, a reduction in flashpoint, and broader molecular weight distribution (higher dispersion index).

Figure 2:
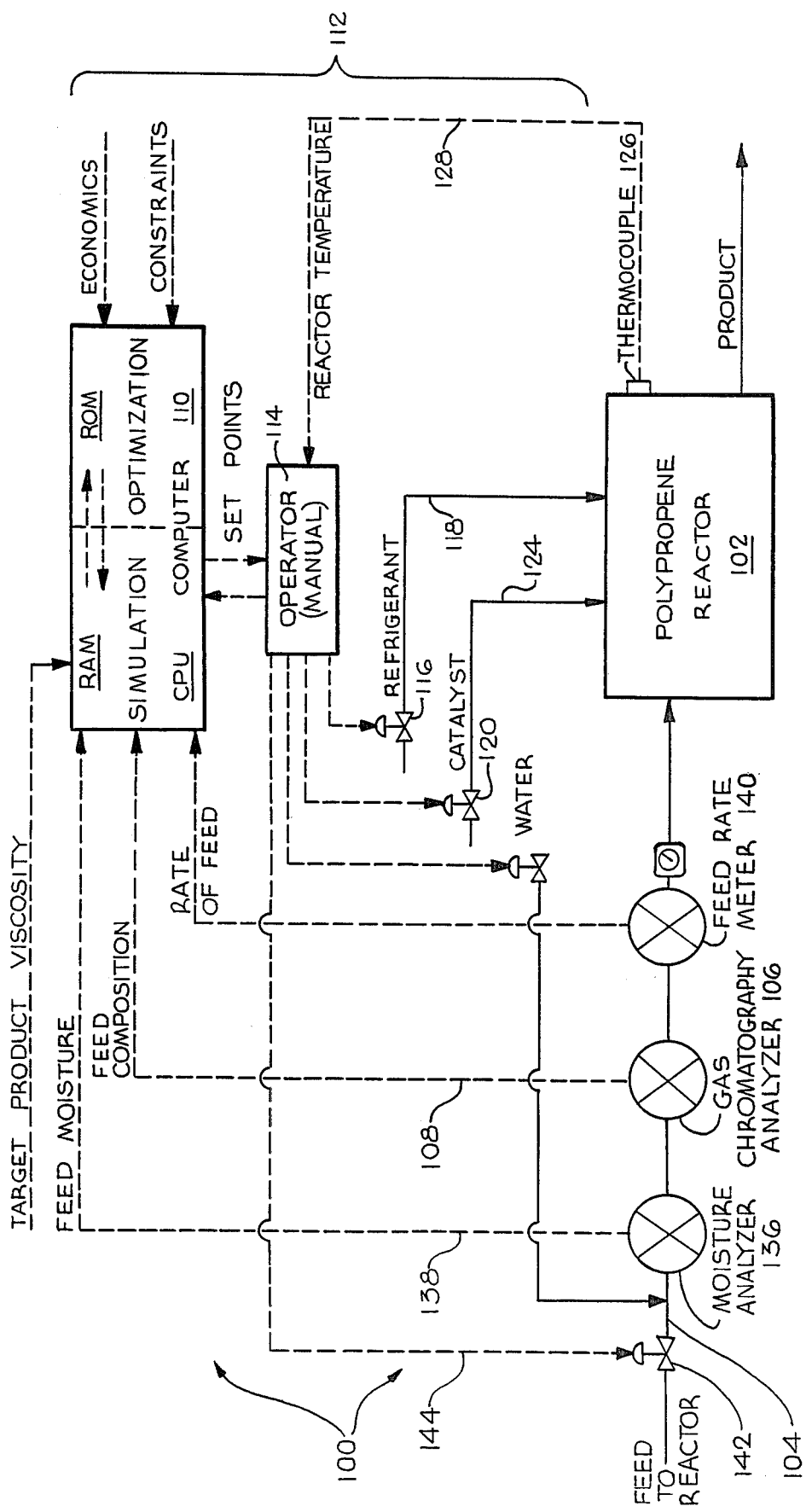
FIG. 2 is a block diagram of an apparatus or system according to the present invention in which the control of water and residence time can be utilized to control the molecular weight of the product output from a polypropene reactor.

A more detailed realization of the method and apparatus of the present invention is shown in FIG. 2. Here a polypropene reactor system 100 includes a polypropene reactor 102 which is supplied with a propylene containing feedstream via feed inlet line 104 and feed valve 142. This feed stream can be monitored by a gas chromatography analyzer 106 which is coupled to the feed input line 104. Additionally a moisture analyzer 136 is provided in the input feed line 204 for determining the amount of moisture in the feed, and a feed rate meter 140 is provided for purposes of monitoring the reactor residence time in conjunction with gas chromatography analyzer 106. The feed composition, as determined by the gas chromatography analyzer 106, is supplied via an electrical circuit 108 to a computer 110. The feed moisture value as determined by the moisture analyzer 136 is fed to computer 110 via an electrical circuit 138. The feed flow rate can be fed to the computer via an electrical circuit 146.

The computer 110 is part of a control system 112 which can be partially manual and partially automatic, and once initial operating constraints are established manually, the computer 110 can operate the reactor system 100 automatically. In this respect, the computer 110 and control circuit 112 comprise a RAM, a ROM and a CPU and a keyboard operator panel 114 by which an operator can set the initial reactor temperature, the initial amount of water supplied to the reactor, the reactor residence time, and the initial amount of catalyst supplied to the reactor. In the system 100 water supplied to the polypropene reactor 102 can be controlled through a valve 132 and water input line 139. Similarly, the flow of refrigerant can be controlled through valve 116, and the flow of catalyst through valve 120.

The panel 114 is coupled to the computer 110 for receiving set points from the computer 110 or manually from the operator and for supplying the computer with data on temperature of the reactor 102 as measured by thermocouple 126 coupled to the reactor which supplies temperature signal via circuit 128, information on the refrigerant being supplied to the reactor, the amount of catalyst being supplied to the reactor, and the residence time of the feed in the reactor.

In conjunction with the teachings of the present invention, an empirical model or simulation can be effective in evaluating the outcome brought about by changing one or more variables in the polypropene system 100. In this respect, an equation can be derived from experimental data and used to predict the molecular weight of a polypropene product output, as a function of reaction temperature, concentration of various olefins in the feed, water levels in the feed, reactor residence time, etc. An empirical equation can be used to predict product grade immediately from reaction conditions.

The computer 110 is also supplied with a target viscosity and any additional economic factors and operation constraints. Given the feed moisture, residence time, reactor temperature, catalyst flow rate and or other operating variables being fed to the computer 110 as described above, the computer, utilizing an empirically determined formula which correlates product viscosity or molecular weight with the operating variable described above, can predict the molecular weight of the polypropene and determine any deviation from the target viscosity.

Figure 3:
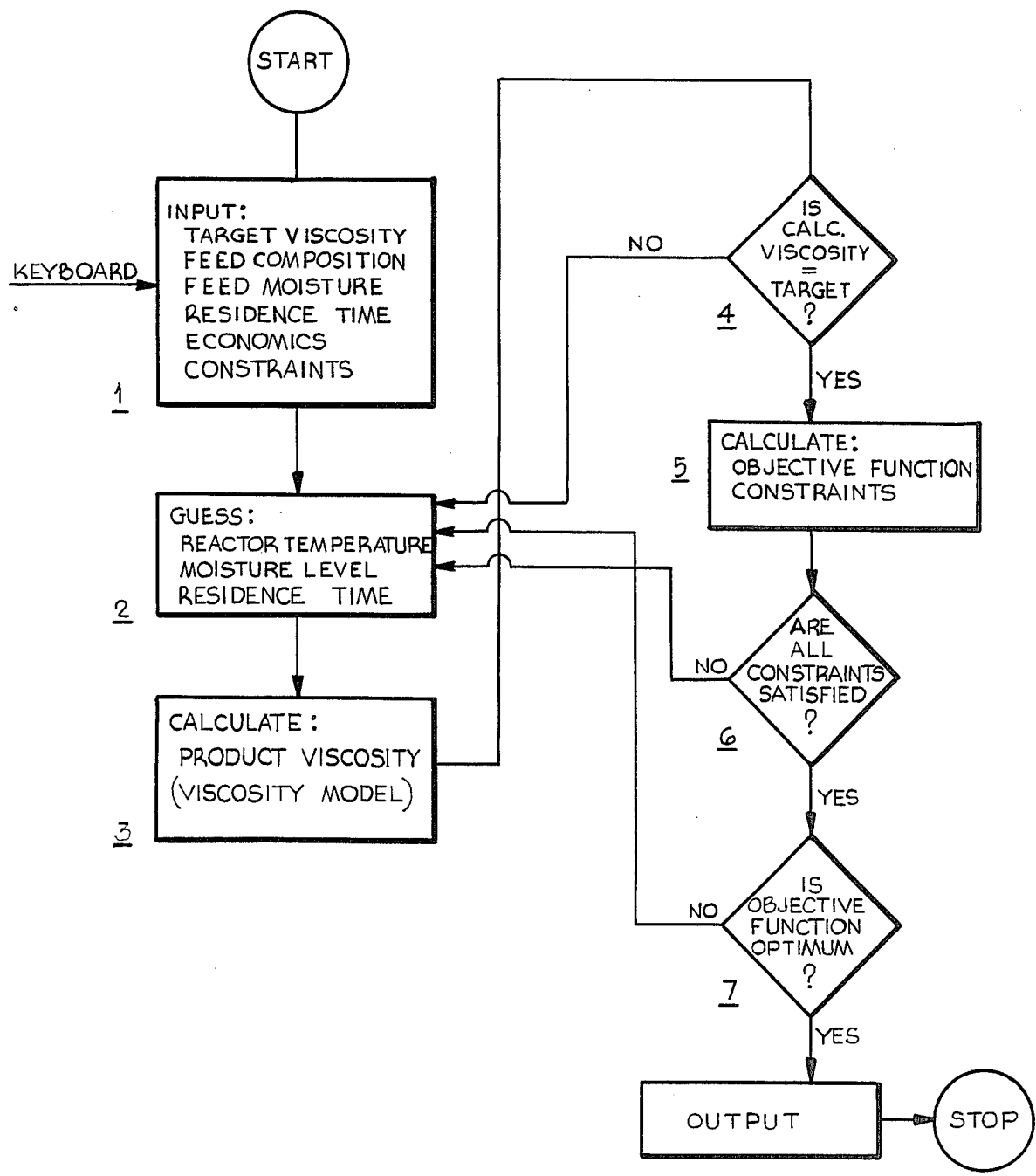
FIG. 3 is a flow chart of a program which can be carried out by the computer in FIG. 2.

Referring now to FIG. 3, there is illustrated therein a flow chart of a program protocol or routine that can be carried out in and by the computer 110 in controlling the polymer product output from the polypropene reactor 102. The routine includes the following steps:

STEP 1. As shown, the polypropene production system 100 is first started up and then at the first step an operator will plug in various inputs such as target viscosity, the feed composition, the feed moisture, the residence time and economic factors and operation constraints.

STEP 2. Here a first reactor temperature is estimated by the computer, sensed by the computer, sensed by the thermocouple 126 or input manually by the operator. In addition, a first moisture level in the feed is estimated by the computer 110, sensed by the moisture analyzer 136 or input manually by the operator. Similarly, a reactor residence time is estimated by the computer, sensed by the feed flow meter in conjunction with the gas chromatography analyzer, or input manually by the operator.

STEP 3. Here the computer calculates, using the empirically derived equation stored in the microprocessor of the computer, a product viscosity.

STEP 4. Here the computer determines whether the calculated viscosity for the temperature, moisture level, and residence time or other variables is equal to the target viscosity. If NO the computer cycles back to step 2 to make new estimations of reactor temperature, feed moisture and residence time, and then proceeds once again through Steps 3 and 4.

STEP 5. When the calculated viscosity equals approximately the target viscosity, the computer 110 goes on to Step 5 where an objective function such as operating cost, and operation constraints such as refrigeration compressor load are calculated. Equipment constraints are also evaluated in this step.

STEP 6. At step 6, the computer determines whether all the constraints are satisfied. If not, it loops back to Step 2.

STEP 7. At Step 7, the computer determines whether the objective function is optimal. In NO, the program loops back to Step 2. If YES, the output is predicted to have, or determined to have, the target viscosity. Here the computer 110 then exits the routine.

Prior to the present invention, if the calculated molecular weight were lower than the target value, one step would have been to lower the reactor temperature or decrease the amount of isobutylene in the feed relative to the amount of propylene. However, lowering the reactor temperature would have involved increased energy costs in terms of refrigeration. Also, increasing propylene relative to isobutylene would also have been undesirable if propylene was more expensive than isobutylene.

Now, according to the present invention, it has been discovered that the molecular weight and viscosity of the polypropene product output can be changed in a controlled fashion by either intentionally changing the moisture level of the feed (or reactor) and/or the reactor residence time. Specifically, increasing the moisture or residence time increases molecular weight, while a reduction in molecular weight can be brought about by decreasing the feed moisture or reactor residence time.

Conventional regression analysis techniques (see, e.g., Daniel et al "Fitting Equations to Data-Computer Analysis of Multifactor Data," Wiley & Sons (1980)) were utilized to determine from the following forty experimental runs which factors effect the molecular weight of the polypropene product. In addition to the feed concentration of isobutylene, cis-2-butene, and the reactor temperature, which were previously known to affect product molecular weight in polypropene manufacture, regression analysis on the data below determined that the moisture content of the feed (or reactor) and the reactor residence time also exert an effect on product molecular weight.

| EXAMPLE | I | II | III | IV | V | VI | VII | VIII | IX | X | XI | XII | XIII | XIV |
|---|---|---|---|---|---|---|---|---|---|---|---|---|---|---|
| Reaction Temp. (°F.) | 136.0 | 134.6 | 134.7 | 92.7 | 93.0 | 134.0 | 135.2 | 135.3 | 135.2 | 134.2 | 134.0 | 74.9 | 85.5 | 40.7 |
| Residence Time (Min) | 88.5 | 121 | 119.8 | 92.3 | 87.5 | 88.6 | 88.2 | 85.1 | 83.9 | 116.3 | 65.0 | 64.8 | 61.5 | 80.6 |
| AlCl₃ (wt. %) | | | | | | | | | | | | | | |
| In Feed | .2440 | .4680 | .4730 | .5150 | .4940 | .5270 | .5110 | .4180 | .4820 | .4770 | .4250 | .4930 | .4450 | .4350 |
| In Reactor | .1860 | .2890 | .2720 | .4220 | .3500 | .3930 | .3700 | .2810 | .3500 | .3790 | .3130 | .3650 | .2930 | .2830 |
| Feed Moisture (ppm) | 138.5 | 171.9 | 159.3 | 237.9 | 200.1 | 204.9 | 196.5 | 189.4 | 204.5 | 221.6 | 207.03 | 6.8 | 247.0 | 247.5 |
| Feed Moisture (ppm, Reactor) | 181.6 | 277.3 | 276.7 | 289.3 | 281.2 | 273.5 | 270.5 | 281.4 | 280.0 | 277.9 | 281.1 | 9.1 | 163.3 | 163.3 |
| Feed Composition | | | | | | | | | | | | | | |
| Nitrogen, Ethylene | 0.29 | 17.29 | 17.78 | 22.94 | 33.43 | 0.21 | 0.19 | 21.14 | 21.23 | 18.40 | .53 | 0.19 | 0.00 | 0.00 |
| Propane | 65.50 | 34.10 | 35.18 | 45.64 | 66.21 | 38.57 | 35.42 | 41.86 | 42.00 | 36.54 | 63.49 | 68.60 | 34.35 | 34.35 |
| Propylene | 0.06 | 4.18 | 3.37 | 0.20 | 0.33 | 3.56 | 4.38 | 2.13 | 2.07 | 7.13 | 0.00 | 0.00 | 65.32 | 65.32 |
| Isobutane | 34.14 | 14.59 | 13.61 | 31.20 | 0.02 | 23.43 | 28.48 | 16.99 | 16.72 | 3.34 | 25.18 | 31.19 | 0.33 | 0.33 |
| N—Butane | 0.00 | 9.69 | 9.65 | 0.00 | 0.00 | 10.86 | 10.06 | 5.72 | 5.56 | 9.93 | 0.00 | 0.00 | | |
| Butene-1 | 0.00 | 14.40 | 14.75 | 0.00 | 0.00 | 16.83 | 15.01 | 8.75 | 8.54 | 17.87 | 10.80 | 0.00 | | |
| Isobutylene | 0.02 | 3.42 | 3.43 | 0.00 | 0.00 | 4.10 | 4.19 | 2.15 | 2.13 | 4.02 | 0.00 | 0.00 | | |
| Trans-Butene-2 | 0.00 | 2.29 | 2.19 | 0.00 | 0.00 | 2.42 | 2.24 | 1.22 | 1.13 | 2.74 | 0.00 | 0.00 | | |
| Cis-Butene-2 | | | | | | | | | | | | | | |
| Inerts | 38.70 | | | | | | | | | | | | 34.68 | 34.68 |
| Totals | 100.00 | 100.00 | 100.00 | 100.00 | 100.00 | 100.00 | 100.00 | 100.00 | 100.00 | 100.00 | 100.00 | 100.00 | 100.00 | 100.00 |
| Reactor Eff. Comp. (wt. % Normalized for Polymer) | | | | | | | | | | | | | | |
| Nitrogen, Ethylene | .51 | 24.04 | 21.64 | 23.33 | 33.43 | .34 | 0.29 | 21.14 | 24.64 | 18.40 | 0.36 | 0.37 | 0.06 | 0.06 |
| Propane | 3.71 | 1.83 | 2.12 | 0.90 | 1.79 | 2.94 | 3.26 | 1.63 | 2.62 | 3.51 | 4.36 | 24.34 | 34.35 | 34.35 |
| Propylene | 0.41 | 4.13 | 3.71 | 0.27 | 0.37 | 4.03 | 4.73 | 2.11 | 2.28 | 6.71 | 0.00 | 0.00 | 1.63 | 3.48 |
| Isobutane | 34.14 | 14.59 | 13.61 | 31.20 | 0.16 | 23.43 | 28.48 | 16.08 | 16.72 | 3.04 | 25.18 | 31.19 | 0.40 | 0.31 |
| N—Butane | 0.00 | 0.70 | 0.84 | 0.00 | 0.00 | 1.14 | 1.33 | 0.31 | 0.47 | 1.33 | 0.00 | 0.00 | 0.15 | 0.10 |
| Butene-1 | 0.00 | 0.00 | 0.00 | 0.00 | 0.00 | 0.00 | 0.00 | 0.00 | 0.00 | 0.00 | 0.00 | 0.00 | | |
| Isobutylene | 0.02 | 1.28 | 1.34 | 0.00 | 0.00 | 1.70 | 1.94 | 0.61 | 0.73 | 1.83 | 0.00 | 0.00 | | |
| Trans-Butene-2 | 0.00 | 0.02 | 0.10 | 0.00 | 0.00 | 0.28 | 0.33 | 0.04 | 0.00 | 0.18 | 0.00 | 0.00 | | |
| Cis-Butene-2 | | | | | | | | | | | | | | |
| Totals | 38.70 | 46.60 | 43.30 | 55.70 | 35.70 | 33.80 | 40.30 | 41.90 | 48.10 | 31.30 | 29.90 | 55.90 | 36.59 | 38.31 |
| wt. % Polymer | 61.21 | 53.41 | 56.64 | 44.30 | 64.25 | 66.14 | 59.64 | 58.08 | 51.93 | 64.73 | 70.10 | 44.10 | 63.41 | 61.69 |
| Monomer Conv. % | | | | | | | | | | | | | | |
| Propylene | 94.33 | 94.61 | 93.96 | 98.01 | 97.29 | 92.35 | 90.77 | 96.10 | 93.74 | 90.38 | 32.58 | 0.00 | | 94.67 |
| Isobutane | 0.00 | 0.00 | 0.00 | 0.00 | 0.00 | 0.00 | 0.00 | 1.01 | 0.00 | 5.83 | 93.13 | 64.52 | .50 | 5.98 |
| Butene-1 | 0.00 | 92.73 | 91.26 | 0.00 | 0.00 | 89.46 | 86.72 | 94.49 | 94.49 | 86.59 | 0.00 | 0.00 | .00 | |
| Isobutylene | 0.00 | 100.00 | 100.00 | 0.00 | 0.00 | 100.00 | 100.00 | 100.00 | 100.00 | 100.00 | 100.00 | 0.00 | | |
| Tran-Butene-2 | 0.00 | 62.42 | 60.78 | 0.00 | 0.00 | 58.31 | 53.72 | 71.64 | 71.64 | 54.30 | 0.00 | 0.00 | | |
| Cis-Butene-2 | 0.00 | 98.96 | 95.03 | 0.00 | 0.00 | 88.16 | 85.26 | 96.59 | 96.53 | 83.35 | 0.00 | 0.00 | | |
| Lbs. Total Polymer Per Lb. Polypropene | .943 | 1.761 | 1.728 | .980 | .973 | 1.729 | 1.696 | 1.364 | 1.323 | 1.751 | 1.101 | .645 | .975 | .947 |
| Lbs. Total Polymer Per Lb. Olefin | .943 | .940 | .932 | .980 | .973 | .916 | .897 | .956 | .935 | .900 | .941 | .645 | .974 | .946 |
| Lbs. Total Polymer Per Lb. Feed | .618 | .601 | .608 | .447 | .644 | .667 | .601 | .571 | .555 | .640 | .699 | .443 | .637 | .618 |
| Material Balance (Overall) | 98.5 | 99.1 | 104.1 | 91.2 | 92.1 | 96.6 | 98.2 | 91.8 | 99.0 | 99.8 | 100.5 | 103.0 | | |
| Material Balance (Total Polymer, GC) | 108.8 | 121.4 | 130.4 | 119.1 | 86.2 | 125.3 | 146.5 | 94.1 | 116.4 | 111.8 | 120.1 | 99.9 | 138.4 | 126.2 |
| Total Polymer Molecular Wt. | | | | | | | | | | | | | | |
| GPC-Mw: | 742 | 481 | 462 | 1,022 | 1,023 | 432 | 453 | 582 | 538 | 459 | 555 | 883 | | |

-continued

| | 563 | 352 | 337 | 737 | 785 | 322 | 338 | 455 | 390 | 347 | 388 | 655 | 839 | 819 |
|---|---|---|---|---|---|---|---|---|---|---|---|---|---|---|
| GPC-$M_n$: | | | | | | | | | | | | | | |
| Heavy Polymer Characteristics | | | | | | | | | | | | | | |
| Selectivity (GPC): | 93.5 | 87.0 | 82.5 | 95.5 | 97.5 | 79.0 | 84.5 | 91.5 | 79.5 | 87.0 | 89.5 | 97.0 | | |
| Selectivity (SD): | 93.8 | 92.3 | 86.0 | 94.7 | 97.4 | 87.1 | 87.0 | 90.0 | 83.4 | 87.3 | 92.8 | 97.0 | | |
| GPC-$M_w$: | 782 | 513 | 525 | 1,047 | 1,015 | 493 | 494 | 617 | 612 | 493 | 613 | 873 | | |
| GPC-$M_n$: | 633 | 417 | 425 | 803 | 808 | 411 | 403 | 503 | 505 | 402 | 490 | 682 | | |
| Flashpoint (COC): | 428.00 | 306.00 | 312.80 | 467.60 | 485.60 | 312.80 | 305.60 | 350.20 | 353.10 | 312.80 | 358 | 435 | 839 | 819 |
| % Unsaturation | 94.0 | 90.7 | 89.7 | 82.3 | 89.0 | 93.2 | 94.8 | 95.0 | 92.8 | 93.7 | 95.4 | 100 | 661 | 656 |
| VPO-$M_n$: | 615 | 378 | 391 | 742 | 813.0 | 383 | 383 | 465 | 476 | 394 | 481 | 703 | 89.8 | 91.2 |
| Viscosity (cst. 210°) | 18.9 | 5.7 | 5.7 | 42.2 | 44.3 | 5.2 | 5.2 | 9.1 | 9.4 | 5.6 | 9.6 | 34.2 | 872 | 992 |
| | | | | | | | | | | | | | 61.2 | 104.2 |

| EXAMPLE | XV | XVI | XVII | XVIII | XIX | XX | XXI | XXII | XXIII | XXIV | XXV | XXVI | XXVII | XXVIII |
|---|---|---|---|---|---|---|---|---|---|---|---|---|---|---|
| Reaction Temp. (°F.) | 125.6 | 121.4 | 35.1 | 85.3 | 84.9 | 75.2 | 75.2 | 129.4 | 144.9 | 144.9 | 74.9 | 59.9 | 44.7 | 139.6 |
| Residence Time (Min) | 82.5 | 95.8 | 93.6 | 61.9 | 64.7 | 63.2 | 64.3 | 77.1 | 76.3 | 55.4 | 71.0 | 65.9 | 69.5 | 79.1 |
| $AlCl_3$ (wt. %) | | | | | | | | | | | | | | |
| In Feed | .3440 | .2750 | .4430 | .4519 | .4280 | .4130 | .4230 | .3350 | .3290 | .3040 | .3280 | .3230 | .3170 | .2560 |
| In Reactor | .2300 | .2130 | .3270 | .2980 | .3000 | .2820 | .2940 | .2110 | .2040 | .1130 | .2480 | .2270 | .2340 | .1630 |
| Feed Moisture (ppm) | 247.2 | 248.6 | 248.4 | 496.0 | 238.4 | 237.3 | 237.8 | 234.0 | 234.2 | 242.6 | 232.8 | 233.4 | 232.1 | 224.2 |
| Feed Moisture (ppm, Reactor) | 165.2 | 193.0 | 189.7 | 328.0 | 167.4 | 162.6 | 166.1 | 147.5 | 146.1 | 106.0 | 176.6 | 164.5 | 172.3 | 143.3 |
| Feed Composition | | | | | | | | | | | | | | |
| Nitrogen, Ethylene | 0.00 | 0.00 | 0.00 | 0.00 | 0.00 | 0.00 | 0.00 | 0.00 | 0.00 | 0.00 | 0.41 | 0.36 | 0.27 | 0.00 |
| Propane | 34.35 | 34.35 | 34.35 | 34.35 | 7.00 | 7.00 | 7.00 | 3.93 | 3.93 | 3.93 | 7.29 | 7.32 | 7.31 | 4.40 |
| Propylene | 65.32 | 65.32 | 65.32 | 65.35 | 68.0 | 68.0 | 68.00 | 58.03 | 58.03 | 58.03 | 66.99 | 67.36 | 67.16 | 51.73 |
| Isobutane | 0.33 | 0.33 | 0.33 | 0.33 | 1.10 | 1.25 | 1.25 | 5.75 | 5.75 | 5.75 | 24.31 | 24.01 | 24.27 | 6.59 |
| Inerts | 34.68 | 34.68 | 34.68 | 34.68 | 23.90 | 23.75 | 23.75 | | | | | | | |
| N—Butane | | | | | | | | 17.96 | 17.96 | 17.96 | | | 0.99 | 17.06 |
| Butene-1 | | | | | | | | 5.10 | 5.10 | 5.10 | | | 0.00 | 7.45 |
| Isobutylene | | | | | | | | 5.52 | 5.52 | 5.52 | | | 0.00 | 7.79 |
| Trans-Butene-2 | | | | | | | | 2.71 | 2.71 | 2.71 | | | — | 3.68 |
| Cis-Butene-2 | | | | | | | | 0.99 | 0.99 | 0.99 | | | | 1.08 |
| Totals | 100.00 | 100.00 | 100.00 | 100.00 | 100.00 | 100.00 | 100.00 | 100.00 | 100.00 | 100.00 | 100.00 | 100.00 | 100.00 | 100.00 |
| Reactor Eff. Comp. (wt. % Normalized for Polymer) | | | | | | | | | | | | | | |
| Nitrogen, Ethylene | 0.06 | 0.05 | 0.07 | 0.05 | 0.00 | 0.00 | 0.00 | 0.00 | 0.00 | 0.00 | 0.53 | 0.61 | 0.63 | 0.54 |
| Propane | 34.35 | 34.35 | 34.35 | 34.35 | 7.00 | 7.00 | 7.00 | 3.93 | 3.93 | 3.93 | 7.29 | 7.32 | 7.31 | 4.40 |
| Propylene | 3.09 | 2.91 | 3.78 | 1.94 | 2.41 | 3.50 | 4.88 | 3.32 | 3.29 | 3.47 | 5.86 | 6.45 | 9.32 | 2.67 |
| Isobutane | 0.29 | 0.32 | 0.40 | 0.32 | 1.13 | 1.25 | 1.25 | 5.75 | 5.75 | 5.75 | 24.31 | 24.01 | 24.27 | 6.59 |
| N—Butane | 0.08 | 0.09 | 0.11 | 0.21 | 23.60 | 23.75 | 23.76 | 17.96 | 17.96 | 17.96 | 1.00 | 0.95 | 1.02 | 17.07 |
| Butene-1 | | | | | | | 0.00 | 0.47 | 0.56 | 0.57 | | | 0.00 | 0.71 |
| Isobutylene | | | | | | | 0.00 | 0.00 | 0.00 | 0.00 | | | 0.00 | 0.00 |
| Trans-Butene-2 | | | | | | | 0.00 | 1.01 | 1.04 | 1.05 | | | 0.00 | 1.54 |
| Cis-Butene-2 | | | | | | | 0.00 | 0.12 | 0.14 | 0.14 | | | 0.00 | 0.06 |
| Totals | 37.86 | 37.72 | 38.71 | 36.89 | 34.14 | 35.49 | 36.88 | 32.57 | 32.67 | 32.88 | 38.99 | 39.34 | 42.54 | 33.58 |
| wt. % Polymer | 62.14 | 62.27 | 61.29 | 63.11 | 65.85 | 64.50 | 63.12 | 67.43 | 67.33 | 67.12 | 61.01 | 60.66 | 57.46 | 66.42 |
| Monomer Conv. % | | | | | | | | | | | | | | |
| Propylene | 95.28 | 95.54 | 94.22 | 97.04 | 96.45 | 94.86 | 92.83 | 94.28 | 94.34 | 94.01 | 91.25 | 90.42 | 86.13 | 94.83 |
| Isobutane | 13.19 | 3.31 | 0.00 | 2.66 | | | 0.00 | 0.00 | 0.00 | 0.00 | | | 0.00 | 0.00 |
| Butene-1 | | | | | | | 4.88 | 90.75 | 89.01 | 88.82 | | | 0.00 | 90.43 |
| Isobutylene | | | | | | | 1.25 | 100.00 | 100.00 | 100.00 | | | 0.00 | 100.00 |
| Trans-Butene-2 | | | | | | | 0.00 | 62.76 | 61.65 | 61.47 | | | 0.00 | 58.03 |
| Cis-Butene-2 | | | | | | | 0.00 | 87.74 | 85.78 | 85.76 | | | 0.00 | 94.43 |
| Lbs. Total Polymer | .953 | .955 | .942 | .970 | .965 | .949 | .928 | 1.162 | 1.160 | 1.157 | .912 | .904 | .861 | 1.290 |

-continued

| EXAMPLE | XXIX | XXX | XXXI | XXXII | XXXIII | XXXIV | XXXV | XXXVI | XXXVII | XXXVIII | XXXIX | XL |
|---|---|---|---|---|---|---|---|---|---|---|---|---|
| Per Lb. Polypropene | .952 | .955 | .941 | .970 | .965 | .949 | .928 | .932 | .931 | .928 | .905 | .896 | .852 | .923 |
| Lbs. Total Polymer | | | | | | | | | | | | | | |
| Per Lb. Olefin | .622 | .624 | .615 | .634 | .656 | .645 | .631 | .674 | .673 | .671 | .611 | .609 | .578 | .667 |
| Per Lb. Total Polymer | | | | | | | | | | | | | | |
| Material Balance | 126.2 | 119.6 | 115.1 | 132.45 | 139.2 | 133.4 | 139.2 | 130.0 | 131.4 | 148.7 | 146.5 | 151.3 | 149.0 | 138.8 |
| (Total Polymer, GC) | | | | | | | | | | | | | | |
| Heavy Polymer Characteristics | | | | | | | | | | | | | | |
| Selectivity: | | | | | | | | | | | | | | |
| GPC-M$_w$: | 839 | 819 | | 1,039 | 1,009 | 1,043 | 1,061 | 685 | 661 | 661 | 948 | 1,045 | 1,087 | 95.6 |
| GPC-M$_n$: | 661 | 656 | 1,039 | 836 | 799 | 830 | 836 | 569 | 550 | 547 | 753 | 832 | 600 |
| Flashpoint (COC) | | | | | | 505 | 496 | 417 | 396 | | | 489 | 852 | 489 |
| % Unsaturation | 91.2 | 91.8 | 1,039 | 89.7 | 87.5 | 90.4 | 92.9 | 91.6 | 94.2 | 94.8 | 95.3 | 49.5 | 504 | 307 |
| VPO-M$_n$: | 667 | 640 | 1,050 | 826 | 822 | 861 | 873 | 562 | 540 | 530 | 822 | 95.9 | 94.1 | 92.9 |
| Viscosity (cst. 210°) | 26.0 | 25.2 | 94.5 | 58.7 | 51.8 | 61.9 | 67.6 | 15.1 | 13.1 | 13.0 | 53.1 | 888 | 888 | 483 |
| | | | 112.5 | | | | | | | | | 7.35 | 83.3 | 10.9 |

| EXAMPLE | XXIX | XXX | XXXI | XXXII | XXXIII | XXXIV | XXXV | XXXVI | XXXVII | XXXVIII | XXXIX | XL |
|---|---|---|---|---|---|---|---|---|---|---|---|---|
| Reaction Temp. (°F.) | 130.0 | 116.0 | 135.5 | 98.9 | 88.2 | 110.4 | 110.2 | 90.6 | 61.9 | 61.5 | 61.6 | 61.5 |
| Residence Time (Min) | 123.2 | 79.0 | 80.3 | 79.6 | 79.5 | 102.4 | 101.3 | 104.7 | 126.4 | 128.0 | 122.5 | 128.0 |
| AlCl$_3$ (wt. %) | | | | | | | | | | | | |
| In Feed | .2510 | .3400 | .3630 | .3350 | .2860 | .2880 | .2740 | .2570 | .4185 | .3917 | .3796 | .3895 |
| In Reactor | .1410 | .2830 | .3010 | .2770 | .2400 | .2340 | .2210 | .2120 | .2092 | .2886 | .2501 | .2082 |
| Feed Moisture (ppm) | 156.0 | 249.5 | 248.9 | 247.5 | 243.1 | 253.3 | 247.7 | 246.1 | 251.5 | 121.8 | 66.6 | 74.7 |
| Feed Mositure (ppm, Reactor) | 87.9 | 207.9 | 207.3 | 205.1 | 204.2 | 206.9 | 200.4 | 203.9 | 126.0 | 90.0 | 44.0 | 40.0 |
| Feed Composition | | | | | | | | | | | | |
| Ethane-Ethylene | 0.42 | 1.13 | 1.06 | 1.29 | 1.29 | 1.14 | 1.27 | 1.29 | | | | |
| Nitrogen, Ethylene | 4.38 | 0.00 | 0.00 | 0.00 | 0.00 | 0.06 | 0.09 | 0.08 | | | | |
| Propane | 52.22 | 78.54 | 81.35 | 75.96 | 75.96 | 53.18 | 51.08 | 53.15 | | | | |
| Propylene | 6.38 | 20.31 | 17.57 | 22.72 | 22.72 | 22.82 | 22.92 | 22.71 | | | | |
| Isobutane | 16.82 | 0.00 | 0.00 | 0.00 | 0.00 | 2.09 | 2.20 | 2.05 | | | | |
| N—Butane | 7.40 | 0.05 | 0.00 | 0.00 | 0.00 | 5.53 | 5.92 | 5.49 | | | | |
| Butene-1 | 7.68 | 0.00 | 0.00 | 0.00 | 0.00 | 10.85 | 11.56 | 10.76 | | | | |
| Isobutylene | 3.67 | 0.00 | 0.00 | 0.00 | 0.00 | 2.51 | 2.86 | 2.57 | | | | |
| Trans-Butene-2 | 0.00 | 0.00 | 0.00 | 0.00 | 0.00 | 1.51 | 1.47 | 1.22 | | | | |
| Cis-Butene-2 | 1.88 | 0.00 | 0.00 | 0.00 | 0.00 | 0.45 | 0.47 | 0.41 | | | | |
| Totals | 100.00 | 100.00 | 100.00 | 100.00 | 100.00 | 100.00 | 100.00 | 100.00 | | | | |
| wt. % Polymer | 34.08 | 28.40 | 25.50 | 29.50 | 30.30 | 33.50 | 33.60 | 31.80 | | | | |
| Monomer Conv. % | 65.92 | 72.03 | 74.50 | 70.47 | 69.68 | 66.54 | 66.41 | 68.17 | | | | |
| Reactor Eff. Comp. | | | | | | | | | | | | |
| (wt. % Normalized for Polymer) | | | | | | | | | | | | |
| Ethane-Ethylene | 0.00 | 0.81 | 0.78 | 0.75 | 0.76 | 0.73 | 0.81 | 0.58 | 0.35 | 0.24 | 0.22 | 0.20 |
| Nitrogen, Ethylene | 0.49 | 0.27 | 0.25 | 0.24 | 0.26 | 0.27 | 0.26 | 0.25 | | | | |
| Propane | 4.38 | 7.00 | 6.90 | 5.82 | 6.58 | 4.96 | 4.78 | 4.04 | | | | |
| Propylene | 3.30 | 20.31 | 17.57 | 22.72 | 22.72 | 22.82 | 22.92 | 22.71 | 22.57 | 22.57 | 22.57 | 22.57 |
| Isobutane | 6.38 | 0.05 | 0.00 | 0.00 | 0.00 | 1.78 | 1.89 | 1.82 | 2.40 | 5.47 | 11.81 | 23.76 |
| N—Butane | 16.82 | 0.00 | 0.00 | 0.00 | 0.00 | 0.94 | 0.99 | 0.80 | 0.14 | 0.00 | 0.02 | 0.08 |
| Butene-1 | 0.78 | 0.00 | 0.00 | 0.00 | 0.00 | 0.00 | 0.00 | 0.00 | | | | |
| Isobutylene | 0.00 | 0.00 | 0.00 | 0.00 | 0.00 | 1.51 | 1.47 | 1.22 | | | | |
| Trans-Butene-2 | 1.88 | 0.00 | 0.00 | 0.00 | 0.00 | 0.45 | 0.47 | 0.41 | | | | |
| Cis-Butene-2 | | | | | | | | | | | | |
| Totals | 34.08 | 28.40 | 25.50 | 29.50 | 30.30 | 33.50 | 33.60 | 31.80 | | | | |
| wt. % Polymer | 65.92 | 72.03 | 74.50 | 70.47 | 69.68 | 66.54 | 66.41 | 68.17 | | | | |
| Monomer Conv. % | | | | | | | | | | | | |
| Ethane-Ethylene | | | | | | | | | 0.00 | 0.00 | 8.54 | 16.45 |

-continued

| | | | | | | | | | | | | |
|---|---|---|---|---|---|---|---|---|---|---|---|---|
| Propylene | 93.68 | 91.08 | 91.50 | 92.33 | 91.33 | 90.65 | 90.64 | 92.38 | 96.89 | 92.92 | 84.70 | 69.22 |
| Isobutane | 0.00 | 0.00 | 0.00 | 0.00 | 0.00 | 0.00 | 0.00 | 0.00 | | | | |
| Butene-1 | 89.42 | 0.00 | 0.00 | 0.00 | 0.00 | 82.92 | 83.28 | 85.31 | | | | |
| Isobutylene | 100.00 | 0.00 | 0.00 | 0.00 | 0.00 | 100.00 | 100.00 | 100.00 | | | | |
| Trans-Butene-2 | 48.68 | 0.00 | 0.00 | 0.00 | 0.00 | 39.84 | 48.65 | 52.54 | | | | |
| Cis-Butene-2 | 96.26 | 0.00 | 0.00 | 0.00 | 0.00 | 74.54 | 76.84 | 77.76 | | | | |
| Lbs. Total Polymer Per Lb. Polypropene | 1.264 | .911 | .915 | .923 | .913 | 1.241 | 1.288 | 1.267 | .969 | .929 | .847 | .692 |
| Lbs. Total Polymer Per Lb. Olefin | 1.264 | .911 | .915 | .923 | .913 | .893 | .895 | .912 | .964 | .926 | .845 | .691 |
| Lbs. Total Polymer Per Lb. Feed | .660 | .715 | .745 | .701 | .694 | .660 | .658 | .674 | .748 | .717 | .654 | .535 |
| Material Balance (Total Polymer, GC) | 140.8 | 130.0 | 119.3 | 141.5 | 129.6 | 133.7 | 129.5 | 130.8 | 123.0 | 123.9 | 97.2 | 187.2 |
| Heavy Polymer Characteristics | | | | | | | | | | | | |
| Selectivity: | 95.6 | — | | | | | | | | | | |
| GPC-$M_w$: | 609 | 884 | 834 | 970 | 1,003 | 662 | 652 | 708 | 1,011 | 834 | 807 | 823 |
| GPC-$M_n$: | 499 | 712 | 681 | 785 | 811 | 548 | 605 | 578 | 726 | 657 | 628 | 637 |
| Flashpoint (COC): | 370 | 446 | 428 | 458 | 475 | 379 | 369 | 387 | | | | |
| % Unsaturation | 95.0 | 89.4 | 90.8 | 93.2 | 91.0 | 94.1 | 93.0 | 93.0 | 91.0 | 98.0 | 91.0 | 97.0 |
| VPO-$M_n$: | 500 | 684 | 633 | 740 | 778 | 513 | 500 | 538 | 916 | 835 | 806 | 800 |
| Viscosity (cst. 210°) | 11.8 | 30.2 | 22.8 | 39.6 | 45.2 | 12.67 | 11.85 | 15.57 | 82.0 | 60.9 | 54.2 | 53.0 |

We claim:

1. Continuous Friedel-Crafts polymerization of propylene based feedstock in a polypropene reactor system to obtain viscous polypropene having a viscosity within the range of about 2 to about 200 centistokes, comprising: (a) continuously injecting water into the feed or the reactor at a monitored and controlled rate and (b) periodically increasing or decreasing the rate of water injection in response to deviations in the molecular weight of the polypropene product from a desired molecular weight.

2. The process of claim 1 wherein the catalyst is $AlCl_3$.

3. The process of claim 1 wherein the polymerization is carried out at a temperature in the range of from about 45° to about 200° F.

4. The process of claim 1 wherein the polymerization is carried out at a temperature within the range of about 60° to about 140° F., and at a pressure of from about 125 to about 200 psi.

5. The process of claim 1 wherein the rate of water injection is controlled such that the water level in the feed or reactor is within the range of from about 10 ppm to about 500 ppm by weight of the feed.

6. The process of claim 5 wherein the water level is from about 100 to about 300 ppm.

7. The process of claim 1 wherein the feed concentration of isobutylene is controlled to within the range of from about 0 to about 25 wt%.

8. The process of claim 7 wherein the feed concentration of cis-2-butene is controlled to within the range of from about 0 to about 5 wt%.

9. The process of claim 1 further comprising the step of periodically increasing or decreasing the residence time of the feed in the reactor in response to deviations in the molecular weight of the polypropene product from a desired molecular weight.

10. A method for controlling the molecular weight of viscous polypropene product during continuous Friedel-Crafts polymerization of propylene-based feed in a polypropene reactor system, the method comprising: (a) continuously injecting water into the feed or the reactor at a monitored and controlled rate; (b) determining the water content in the feed or reactor; (c) calculating a predicted molecular weight or viscosity of polypropene product based upon an empirically derived formula correlating reactor system operating variables comprising feed or reactor water content to product viscosity or molecular weight to determine if such predicted molecular weight or viscosity is equal to a desired molecular weight or viscosity; and (d) increasing or decreasing the rate of water injection into the feed or reactor such that the predicted product viscosity or molecular weight is equal to the desired viscosity or molecular weight.

11. The method of claim 10 wherein the water content is increased to increase the product molecular weight or reduced to lower the molecular weight.

12. The method of claim 10 wherein the polymerization catalyst is $AlCl_3$.

13. The method of claim 10 wherein polymerization is carried out at a temperature in the range of from about 45° to about 200° F.

14. The method of claim 13 wherein polymerization is carried out at a temperature within the range of about 60° to about 140° F., and at a pressure of from about 125 to about 200 psi.

15. The method of claim 10 wherein the water content is controlled to within the range of from about 10 ppm to about 500 ppm by weight of the feed.

16. The method of claim 15 wherein the water level is from about 100 to about 300 ppm.

17. The method of claim 10 wherein the feed concentration of isobutylene is controlled to within the range of from about 0 to about 20 wt%.

18. The method of claim 17 wherein the feed concentration of cis-2-butene is controlled to within the range of from about 0 to about 5 wt%.

19. The method of claim 10 further comprising the steps of (1) determining the residence time of the feed in the reactor; (2) calculating said predicted product molecular weight or viscosity where said formula correlates residence time to molecular weight or viscosity; and (3) increasing or decreasing the residence time such that the predicted product viscosity or molecular weight equals a desired viscosity or molecular weight.

20. A continuous process for producing viscous polypropene via Friedel-Crafts polymerization of propylene based feed containing up to about 50 wt.% isobutylene by weight of reactive monomers in the feed in a polypropene reactor system wherein the polypropene product is maintained at a target viscosity within the range of about 2 to about 60 centistokes despite periodic changes in the feed isobutylene concentration, the process comprising (a) continuously injecting water into the feed or the reactor at a monitored and controlled rate; (b) periodically increasing or decreasing the feed isobutylene concentration as desired based upon the cost of isobutylene relative to other feed components; and (c) periodically increasing or decreasing the rate of water injection in response to deviations in the polypropene target viscosity caused by said increase or decrease in the feed isobutylene concentration, whereby the polypropene target viscosity is maintained.

21. The process of claim 20 wherein the rate of water injection is increased in response to an increase in the feed concentration of isobutylene.

22. The process of claim 20 wherein the rate of water injection is decreased in response to a decrease in the feed concentration of isobutylene.

23. The process of claim 20 further comprising the step of periodically increasing or decreasing residence time of the feed in the reactor in response to deviations in the polypropene target viscosity caused by said increase or decrease in the feed isobutylene concentration.

24. The process of claim 23 wherein the reactor residence time is increased in response to an increase in the feed concentration of isobutylene.

25. The process of claim 23 wherein the reactor residence time is decreased in response to a decrease in the feed concentration of isobutylene.

* * * * *

UNITED STATES PATENT OFFICE
CERTIFICATE OF CORRECTION

Patent No. 4,777,317  Dated  October 11, 1988

Inventor(s)  Gregory E. Schmidt and James S. Moore

It is certified that error appears in the above-identified patent and that said Letters Patent is hereby corrected as shown below:

Col. Line 2  54  "general object" and should read --a general object--

2  64  "are," and should read --are--

4  64  "on a" and should read --in a--

7  3  "$\approx$" and should read --$\tilde{=}$--

7  4  "$\approx$" and should read --$\tilde{=}$--

7  5  "$\approx$" and should read --$\tilde{=}$--

7  9  "$\approx$" and should read --$\tilde{=}$--

7  10  "$\approx$" and should read --$\tilde{=}$--

UNITED STATES PATENT OFFICE
CERTIFICATE OF CORRECTION

Patent No. 4,777,317  Dated October 11, 1988

Inventor(s)  Gregory E. Schmidt and James S. Moore

It is certified that error appears in the above-identified patent and that said Letters Patent is hereby corrected as shown below:

<u>Col.</u> <u>Line</u>

Exam- 35-36  ".50" and should read --97.50
ple XIII  0.00--
    XXXVII
under/ EXAM-
PLE in 3rd
chart  "Ethan-Ethylene" and should read --Ethane-Ethylene--

EXAMPLE
XXIX  45  "1.264" and should read --.910--

Signed and Sealed this

Eleventh Day of July, 1989

Attest:

DONALD J. QUIGG

Attesting Officer     Commissioner of Patents and Trademarks